United States Patent [19]

Williamson

[11] Patent Number: 4,657,005
[45] Date of Patent: Apr. 14, 1987

[54] GER HARNESS

[76] Inventor: Shirley Williamson, S.R. 4 Box 210, Brightwood, Va. 22715

[21] Appl. No.: 821,971

[22] Filed: Jan. 24, 1986

[51] Int. Cl.⁴ .............................................. A61F 5/37
[52] U.S. Cl. .................................................. 128/134
[58] Field of Search ...................... 128/133, 134, 135; 604/385 A

[56] References Cited

U.S. PATENT DOCUMENTS

| | | | |
|---|---|---|---|
| 2,566,046 | 8/1951 | Weinstein | 128/134 |
| 4,050,737 | 9/1977 | Jordan | 128/134 X |
| 4,117,840 | 10/1978 | Rasure | 128/134 |
| 4,132,229 | 1/1979 | Morrison | 128/134 |
| 4,388,075 | 6/1983 | Mesek et al. | 604/385 X |

OTHER PUBLICATIONS

Brochure entitled "GER Harness", MRI Corporation, Powell, TN 37849, 1984.

Primary Examiner—Richard T. Stouffer
Attorney, Agent, or Firm—Larson and Taylor

[57] ABSTRACT

A harness for infants afflicted with gastroesophageal reflux which secures the infant in position on an inclined surface safely, conveniently and comfortably. This is desirable because positional treatment of this nature is indicated for gastroesophageal reflux.

6 Claims, 2 Drawing Figures

GER HARNESS

FIELD OF THE INVENTION

The present invention relates to an infant's harness to be used for positional treatment of an infant afflicted with gastroesophageal reflux.

BACKGROUND OF THE INVENTION

Gastroesophageal reflux (GER) is a common problem in infants. While in most cases it causes only mild problems for the infant and mother, it can cause serious problems for particular infants. Positional treatment of a child with gastroesophageal reflux is indicated. R. E. Behrman and V. C. Vaughan III, *Nelson Textbook of Pediatrics,* pp. 896-897, (1983). In this treatment the infant is placed in a prone position lying at an angle of inclination to aid the esophageal passage in remaining firm and tight. Positional treatment is employed to allow, with help from gravity, the ingested food to remain in the infant's digestive tract.

Commercially available GER harnesses exist, but they are not without shortcomings that have subjected them to criticism from members of the medical community. One of the major disadvantages of the prior art GER harnesses is that the anti-roll strap must be unfastened to remove the infant from the harness. Since infants afflicted with GER will frequently vomit, it is often necessary to quickly remove the infant from the harness to prevent her from choking.

Another shortcoming of the prior art harness lies in the configuration of the shoulder and anchor straps. This configuration causes a space to be left between these straps near the head of the infant which is just the right size for the infant to get her head caught therein. Further, the shoulder straps must be unfastened to remove the infant from the harness. In an emergency this can be time consuming and dangerous.

Finally, the prior art does not allow for length adjustment of the shoulder strap to comfortably accomodate the infant. Because of this, the prior art harness does not fit snugly about the shoulders of the infant.

Accordingly, an object of the present invention is to provide a GER harness for positional treatment that is safer and more convenient than prior art harnesses.

A further object of the present invention is to provide a GER harness which does not require the unfastening of the anti-roll strap to remove the infant therefrom.

Another object of the present invention is to provide a GER harness which does not require the unfastening of both of the shoulder straps to remove the infant therefrom.

Yet another object of the present invention is to provide a GER harness having adjustable shoulder straps which allow the harness to fit snugly about the shoulders of the infant.

SUMMARY OF THE INVENTION

An infant's harness for positional treatment of an infant afflicted with gastroesophageal reflux comprising;

(i) an elongated body portion having a front side, a back side, and a bottom;

(ii) a pair of anti-roll straps attached to opposite side edges of said back side for preventing rotation of said elongated body portion;

(iii) a pair of waist encircling straps attached to opposite side edges of said back side for securing said elongated body portion around the waist of the infant, (iv) means for releasably attaching said waist encircling straps to one another, (v) a pair of anchor straps attached to the top edge of said back side for anchoring said elongated body portion to an inclined surface, (vi) a pair of shoulder straps attached to the top edge of said front side for securing said elongated body portion around the shoulders of the infant, and (vii) means for releasably attaching said shoulder straps to said anchor straps.

This invention provides a comfortable, convenient, and safe GER harness for securing an infant on an inclined surface, yet permitting rapid removal of the infant from the harness. Also, the harness of the invention allows free and unrestricted movement of the infant's arms and legs while preventing the infant from rolling over.

Furthermore, contrary to prior art harnesses, the anti-roll strap of the present invention by virtue of its attachment to the part of the harness which goes underneath the baby renders unnecessary the unfastening of strap to remove the baby from the harness. This makes removal of the infant from the harness a quick and easy task.

It is to be noted, moreover, that the configuration of the shoulder and anchor straps of the present invention is such that no space between the straps is present. This feature of the invention eliminates the possibility of the infant getting her head caught between the straps. Also, because of the means for fastening the shoulder straps to the anchor straps, the shoulder straps of the present invention are simpler to unfasten than those of the prior art. This is an advantage if an emergency situation should arise which requires hasty removal of the infant from the harness.

Lastly, the means for attaching the shoulder strap to the anchor strap of the present invention allows for adjustment of the length of the shoulder strap. This feature allows the harness to fit snugly yet comfortably around the shoulder of the infant and adds a measure of stability of the harness.

BRIEF DESCRIPTION OF THE DRAWINGS

The invention will be described with reference to the drawing wherein.

DESCRIPTION OF THE PREFERRED EMBODIMENT

Figure 1:
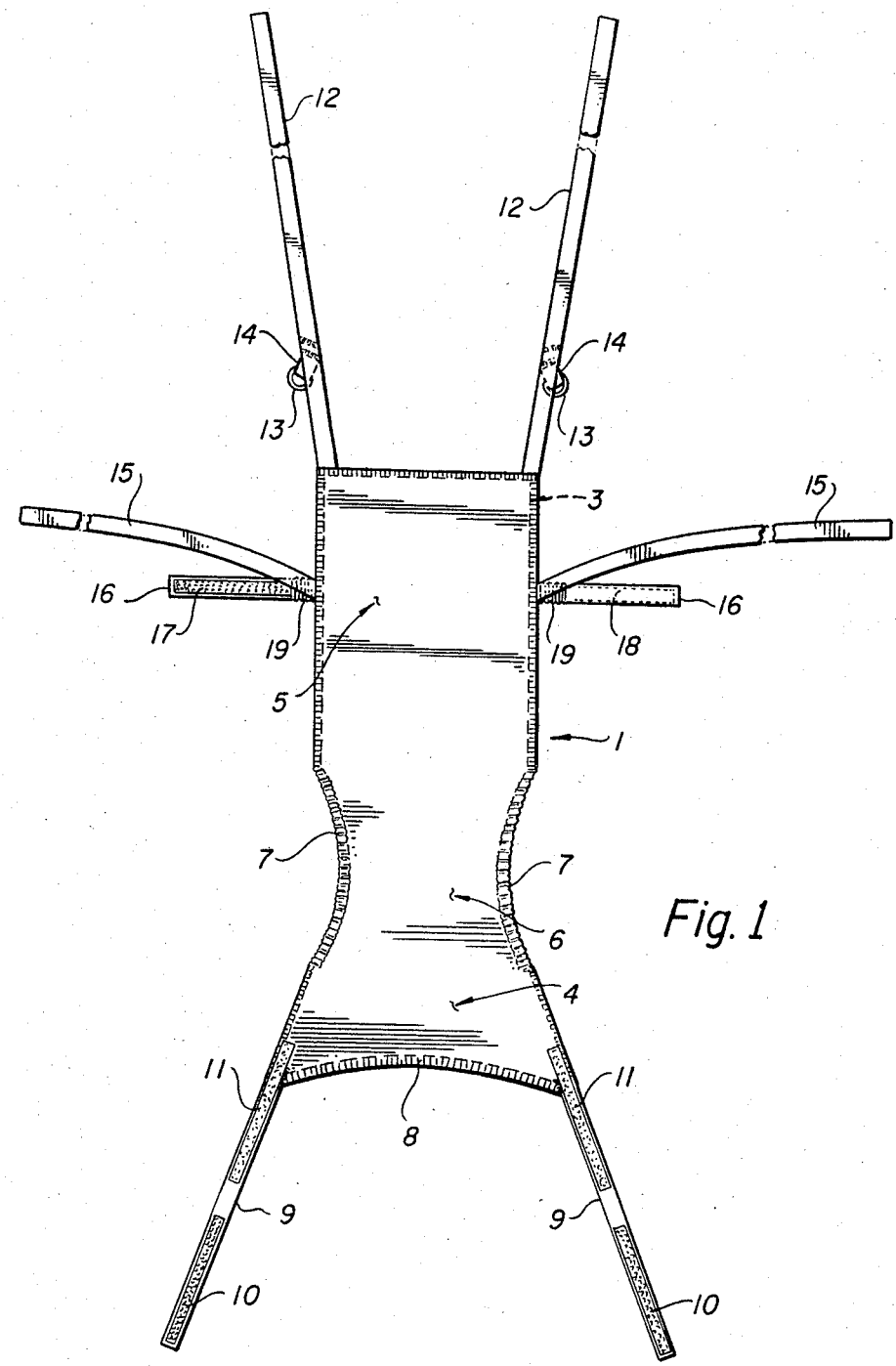
FIG. 1 is a plan view of the GER harness.
Figure 2:
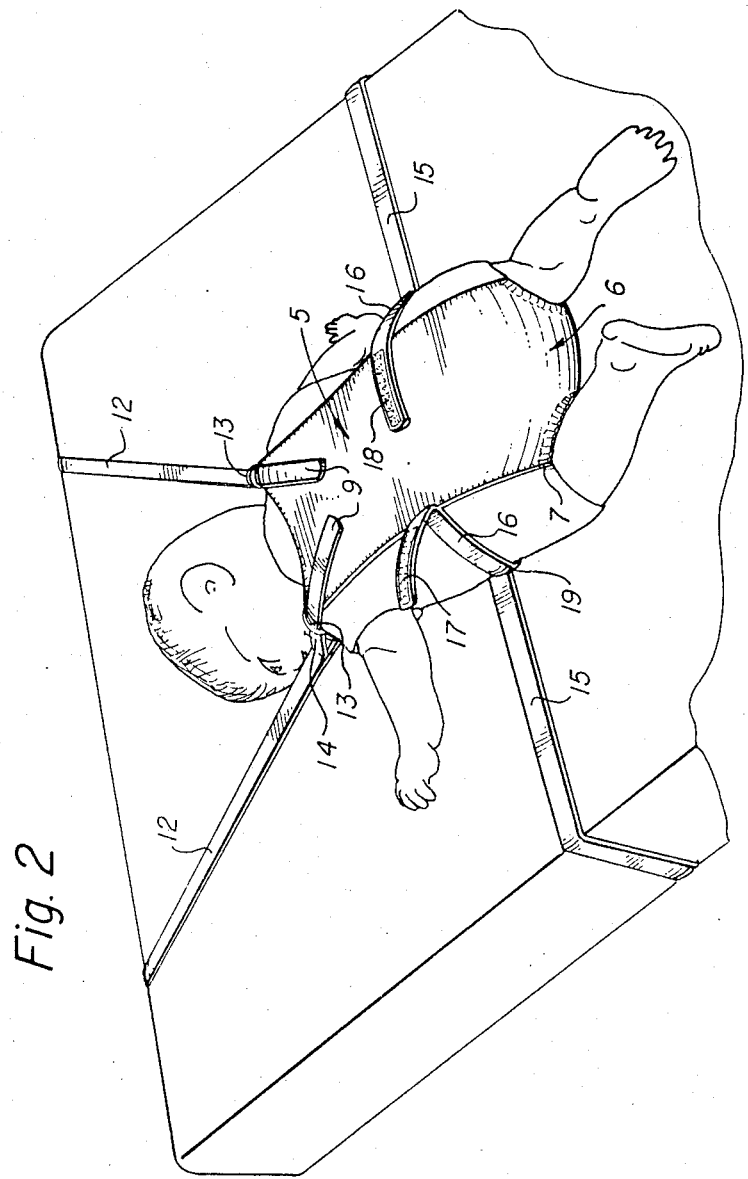
FIG. 2 is a perspective of the GER harness on the infant.

The harness comprises an elongated body portion 1 which covers the torso of the infant. The harness may be made of cotton, wool, or any other material suitable for contact with the skin of an infant. The entire edge of the elongated body 1 may be sewn, to give added strength to the harness, as 3.

The shirt-like body 1 is essentially composed of three main parts; the front side 4, the back side 5, and the bottom 6. The front side 4 comprises the portion of the elongated body 1 which will fit over the back of the infant when the harness is affixed in its working position. The back side 5 will cover the chest, stomach and abdomen of the infant when the harness is affixed in its working position. The bottom portion 6 will cover the infant's crotch and buttocks when the harness is affixed in its working position. The bottom 6 also serves as the connection between the front side 4 and the back side 5. When the harness is affixed in its working position the body 1 will fold over in the middle of the bottom 6 to form the front side 4 and the back side 6.

The bottom 6 is equipped with a pair of flexible gathers 7 which allow the bottom 6 to fit snugly and comfortably about the infant's legs. These flexible gathers 7 may be constructed of an elastic material sewn onto the bottom 6 and covered with an excess of the soft material from which the body 1 is made. These flexible gathers 7 should be elastic enough to adjust to the size of the infant's legs as well as the movements of the infant. This bottom 6 is an improvement over the closest prior art since its width is greater. This greater width will distribute the infant's weight over a larger surface area and thereby make the infant more comfortable in the harness.

The front side 4 has a curved edge 8 which functions as a neck opening for the infant. The front side 4 also includes two shoulder straps 9 which will fit over the shoulder of the infant. These shoulder straps 9 include a male fastener 10 and a female fastener 11 which are preferably made of Velcro. The shoulder straps 9 attach to the anchor straps 12 by being threaded through the rings 13. The shoulder straps 9 then fold over upon themselves usually at a point between the male fastener 10 and the female fastener 11 such that the male fastener 10 comes in contact with, and affixes to the female fastener 11 thereby securing the shoulder straps 9 in position.

The back side 5 is equipped with a pair of anchor straps 12 which are attached to the top edge of the back side 5. These anchor straps 12 are to be pinned to the mattress such that they anchor the harness to the higher portion of the mattress. In other words, the harness essentially hangs down the inclined slope of the mattress on the anchor straps 12. The anchor straps 12 include a pair of rings 13. These rings 13 are hooked through a piece of material 14 sewn onto the anchor straps 12. The rings 13 are for the purpose of threading the shoulder straps 9 through such that the shoulder straps 9 are adjustable as well as manually disengageable.

The back side 5 also has a pair of anti-roll straps 15 attached to opposite edges of the back side 5. These anti-roll straps 15 are to be pinned to the mattress to prevent lateral movement and rolling of the harness with the infant in it. A principle advantage of this harness over the prior art is the attachment of the anti-roll straps 15 to the back side 5 because the anti-roll straps 15 need not be undone to remove the infant from the harness.

The back side 5 has a pair of waist encircling straps 16 attached to opposite edges of the back side 5 as well. The waist encircling straps 16 are to be encircled around the waist of the infant and the male waist strap fastener 17, which is on the top side of one of the waist encircling straps 16, is fastened to the female waist strap fastener 18, which is on the underside of the other waist encircling strap 16, to secure the baby in the harness. These waist encircling straps 16 are to be fastened over the front side 4 of the harness as an added way of securing the harness in place. The waist encircling straps 16 also include an elastic portion 19 which allows the waist encircling straps 16 to be adjusted in their length. These waist encircling straps 16 will fit the waist of the infant in a snug and comfortable manner due to the flexibility of the elastic portion 19. The fastening method of the waist encircling straps 16 allows quick and easy removal of the infant from the harness.

The harness of this invention may be fabricated in several different, custom fit sizes to accommodate infants of varying sizes. The anchor straps 12 and anti-roll straps 15 may be tied to nearly immovable objects rather than pinned to the mattress. The harness will function equally as well in either circumstance.

From the above description it is apparent that the harness may be worn by an infant in a manner which permits comfort as well as free movement of the head, arms, and legs while keeping the infant in the inclined position that is indicated for treatment of GER.

It should be understood that many variations in the harness of the preferred embodiment may be made without impairing the operability of the invention. Therefore, this patent should not be limited to the embodiment exactly as described but shall include all equivalent harnesses which fall within the scope of the claims to follow.

I claim:

1. An infant's harness for positional treatment of an infant afflicted with gastroesophageal reflux comprising;
    (i) an elongated body portion having a front side, a back side, and a bottom;
    (ii) a pair of anti-roll straps attached to opposite side edges of said back side for preventing rotation of said elongated body portion;
    (iii) a pair of waist encircling straps attached to opposite side edges of said back side for securing said elongated body portion around the waist of an infant,
    (iv) means for releasably attaching said waist encircling straps to one another,
    (v) a pair of anchor straps attached to the top edges of said back side for anchoring said elongated body portion to an inclined surface,
    (vi) a pair of shoulder straps attached to the top edge of said front side for releasably securing said elongated body portion around the shoulders of the infant, and
    (vii) adustable means for releasably attaching said shoulder straps to said anchor straps and to said front side, said adjustable means comprising apertured members connected to said anchor straps near where said anchor straps are attached to said back side, said membes each including an aperture of sufficient size for one of said shoulder straps to fit through, said adjustable means further comprising longiudinally spaced interengaging fastener mean on one face of said shoulder straps and on said front side, so that said shoulder straps may fit through said apertured members and said fastener means may interengage to attach said shoulder straps to said anchor straps and to said front side to provide a snug fit of said shoulder and anchor straps around the shoulders of the infant thereby eliminating any space between the shoulder straps and the anchor straps.

2. An infant's harness according to claim 1 wherein said apertured members comprise rings.

3. An infant's harness according to claim 1 wherein said fastener means for releasably attaching said shoulder straps to said anchor straps and to said front side comprises a Velcro fastener.

4. An infant's harness according to claim 1, wherein said elongated body portion comprises flexible gathers along each edge of said bottom.

5. An infant's harness according to claim 1 wherein said waist encircling straps comprise an elastic portion for adjusting the length of said waist encircling straps.

6. An infant's harness according to claim 1 wherein said means for attaching said waist encircling straps to one another comprises a Velcro fastener.

* * * * *